(12) United States Patent
Morikawa

(10) Patent No.: US 11,160,486 B2
(45) Date of Patent: Nov. 2, 2021

(54) ECG WAVEFORM TIMING DETECTOR AND MEDICAL IMAGE DIAGNOSIS APPARATUS

(71) Applicant: Canon Medical Systems Corporation, Otawara (JP)

(72) Inventor: Koichi Morikawa, Otawara (JP)

(73) Assignee: Canon Medical Systems Corporation, Otawara (JP)

( * ) Notice: Subject to any disclaimer, the term of this patent is extended or adjusted under 35 U.S.C. 154(b) by 35 days.

(21) Appl. No.: 16/257,472

(22) Filed: Jan. 25, 2019

(65) Prior Publication Data

US 2019/0223742 A1 Jul. 25, 2019

(30) Foreign Application Priority Data

Jan. 25, 2018 (JP) .............................. JP2018-010236

(51) Int. Cl.
*A61B 5/352* (2021.01)
*A61B 5/00* (2006.01)
*A61B 5/024* (2006.01)
*A61B 5/316* (2021.01)

(52) U.S. Cl.
CPC .............. *A61B 5/352* (2021.01); *A61B 5/024* (2013.01); *A61B 5/316* (2021.01); *A61B 5/7235* (2013.01); *A61B 5/7282* (2013.01); *A61B 5/0006* (2013.01)

(58) Field of Classification Search
CPC ... A61B 5/0456; A61B 5/04012; A61B 5/024; A61B 5/7282; A61B 5/7235; A61B 5/0006
USPC ............................................................ 607/2
See application file for complete search history.

(56) References Cited

U.S. PATENT DOCUMENTS

| | | | | |
|---|---|---|---|---|
| 4,546,777 | A * | 10/1985 | Groch | A61B 7/04 600/528 |
| 5,709,215 | A * | 1/1998 | Perttu | A61B 5/352 600/521 |
| 9,788,742 | B2 * | 10/2017 | Thakur | A61N 1/3706 |
| 2006/0041201 | A1* | 2/2006 | Behbehani | A61B 5/4818 600/521 |
| 2010/0298656 | A1* | 11/2010 | McCombie | A61B 5/02125 600/301 |

(Continued)

FOREIGN PATENT DOCUMENTS

JP 2008-167975 7/2008

*Primary Examiner* — William J Levicky
*Assistant Examiner* — Alexander M Eisenberg
(74) *Attorney, Agent, or Firm* — Oblon, McClelland, Maier & Neustadt, L.L.P.

(57) ABSTRACT

According to one embodiment, an electrocardiographic (ECG) waveform timing detector includes an ECG waveform receiving circuit, a threshold value determining circuit, and a comparator. The threshold value determining circuit includes a heart rate calculating circuit, a threshold value setting circuit, and a comparing/determining circuit. The heart rate calculating circuit calculates the heart rate based on ECG waveform received by the ECG waveform receiving circuit. The threshold value setting circuit sets a threshold value. The comparing/determining circuit compares the heart rate with the number of R wave detection triggers detected using the threshold value to determine a threshold value for R wave detection trigger. The comparator compares the ECG waveform output from the ECG waveform receiving circuit with the threshold value for R wave detection trigger to output an R wave detection trigger.

20 Claims, 16 Drawing Sheets

(56) References Cited

U.S. PATENT DOCUMENTS

| | | | | |
|---|---|---|---|---|
| 2013/0030314 A1* | 1/2013 | Keel | ............... | A61B 5/0464 |
| | | | | 600/518 |
| 2013/0165805 A1* | 6/2013 | Lee | ............. | A61B 5/316 |
| | | | | 600/521 |
| 2013/0190637 A1* | 7/2013 | Zhang | ............. | A61B 5/0456 |
| | | | | 600/521 |
| 2016/0310746 A1* | 10/2016 | Greenhut | ............. | A61B 5/686 |
| 2017/0354827 A1* | 12/2017 | Zhang | ............. | A61B 5/00 |
| 2018/0333058 A1* | 11/2018 | Coulon | ............. | A61B 5/486 |

\* cited by examiner

ECG WAVEFORM TIMING DETECTOR AND MEDICAL IMAGE DIAGNOSIS APPARATUS

CROSS-REFERENCE TO RELATED APPLICATION

This application is based upon and claims the benefit of priority from Japanese Patent Application No. 2018-010236, filed on 2018 Jan. 25; the entire contents of which are incorporated herein by reference.

FIELD

Embodiments described herein relate generally to an electrocardiographic (ECG) waveform timing detector and a medical image diagnosis apparatus.

BACKGROUND

In recent years, a subject is sometimes examined with a medical image diagnosis apparatus that collects information on the inside of a subject and generates a medical image by imaging the inside of the subject based on the information. When the medical image is displayed, an electrocardiogram obtained from a biological signal measuring device such as an electrocardiograph may also be displayed together with the medical image.

Examples of the medical image diagnosis apparatus include ultrasound image diagnosis apparatuses. An ultrasound image diagnosis apparatus receives reflected signals of ultrasound waves transmitted toward a target site to be diagnosed, and generates an ultrasound image relating to the target site. Because of its high temporal resolution, the ultrasound image is suitable for illustrating moving organs such as the heart. The display of an electrocardiogram together with the ultrasound image having such characteristics enables, for example, the phase of the heart's movement to be detected accurately.

X-ray computed tomography (CT) systems may also be cited as examples of the medical image diagnosis apparatus. By using an X-ray CT system, tomographic images of a target site of the subject can be acquired. The movement of the heart can be obtained appropriately by conducting, for example, ECG synchronous reconstruction with the X-ray CT system and the above-mentioned electrocardiograph.

When an electrocardiograph is used, an R wave is often detected and utilized since it has a high wave height and is easy to detect as compared to other waves among those found in an electrocardiogram. Specifically, the interval between R waves is detected as one heartbeat to display an electrocardiogram with an ultrasound image or conduct ECG synchronous reconstruction.

However, it may be difficult to reliably detect R waves every time, and it may happen that, for example, a P wave is erroneously detected as an R wave. One approach to prevent this is to mask detected P waves. Another approach is to emphasize R waves by reducing the amplitude of other waves than R waves such as P waves and T waves with a filter. Still, even these processes cannot ensure the accurate detection of R waves.

DETAILED DESCRIPTION

In general, according to one embodiment, an electrocardiographic (ECG) waveform timing detector includes an ECG waveform receiving circuit, a threshold value determining circuit, and a comparator. The ECG waveform receiving circuit receives an ECG waveform obtained by measuring a subject. The threshold value determining circuit determines a threshold value for R wave detection trigger. The comparator compares the ECG waveform output from the ECG waveform receiving circuit with the threshold value for R wave detection trigger output from the threshold value determining circuit to output an R wave detection trigger. The threshold value determining circuit includes a heart rate calculating circuit, a threshold value setting circuit, and a comparing/determining circuit. The heart rate calculating circuit calculates the heart rate based on the ECG waveform received by the ECG waveform receiving circuit. The threshold value setting circuit sets a threshold value. The comparing/determining circuit compares the heart rate with the number of R wave detection triggers detected using the threshold value to determine the threshold value for R wave detection trigger.

Exemplary embodiments will be described in detail with reference to the drawings.

It is herein assumed that the ultrasound image diagnosis apparatus described below is provided therein with a timing detector. As described above, examples of the medical image diagnosis apparatus include, in addition to ultrasound image diagnosis apparatuses, X-ray CT systems and the like. Accordingly, the timing detector can also be used in such a medical image diagnosis apparatus as an X-ray CT system. However, an ultrasound image diagnosis apparatus is described herein as an example.

[Configuration of Ultrasound Image Diagnosis Apparatus]

Figure 1:
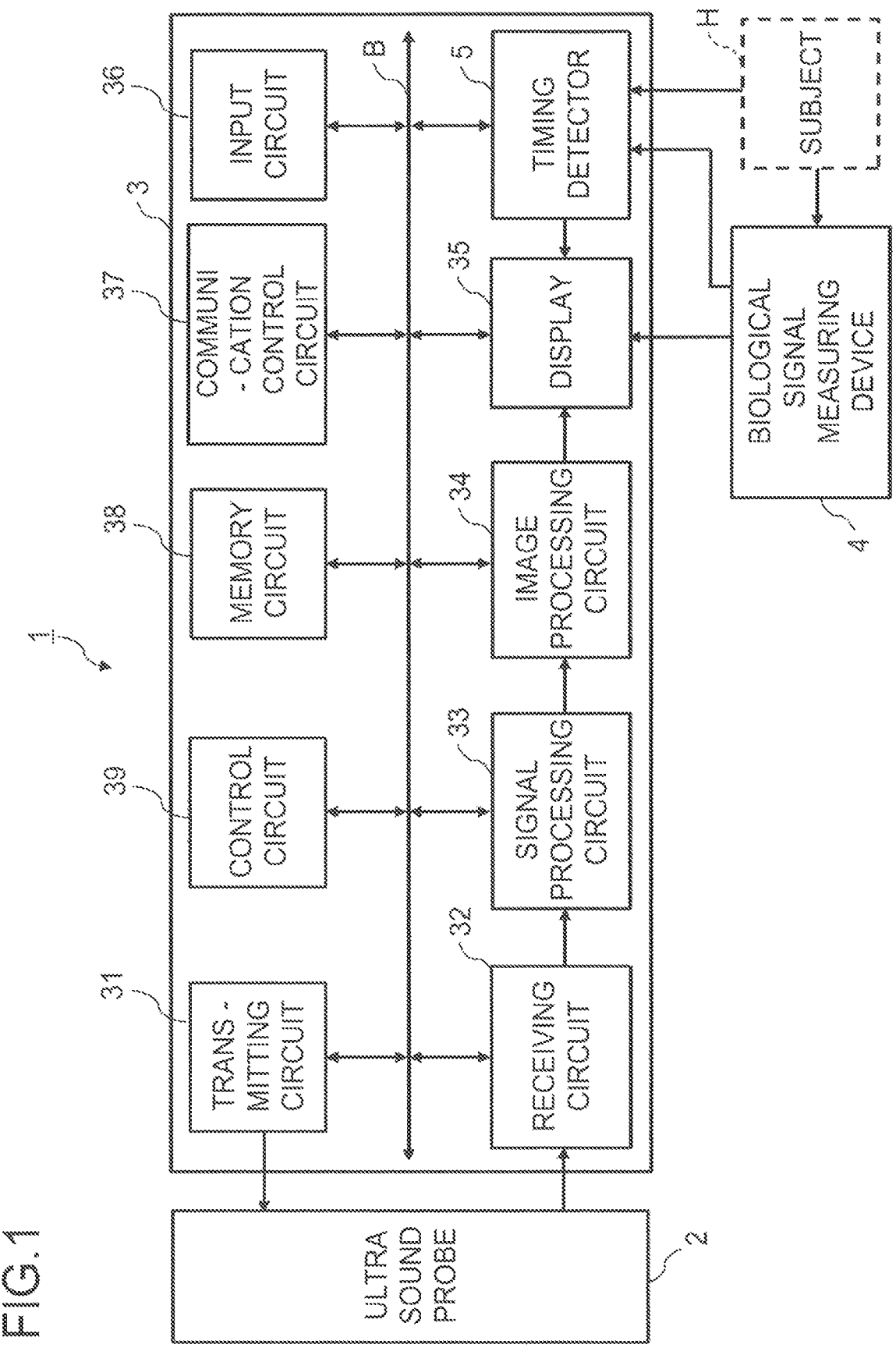
FIG. 1 is a functional block diagram illustrating the overall configuration of a medical image diagnosis apparatus (ultrasound image diagnosis apparatus) according to an embodiment.

FIG. 1 is a functional block diagram illustrating the overall configuration of an ultrasound image diagnosis apparatus 1 according to an embodiment. As illustrated in FIG. 1, the ultrasound image diagnosis apparatus 1 includes an ultrasound probe 2 configured to transmit and receive ultrasound waves to and from a subject, and a main body 3. The ultrasound probe 2 is detachably connected to the main body 3. Besides, the ultrasound image diagnosis apparatus 1 is connected to an electrocardiograph as a biological signal measuring device 4, and receives signals from the biological signal measuring device 4.

In this example, the biological signal measuring device 4 is connected to the ultrasound image diagnosis apparatus 1 as a separate device. However, for example, the functions of the biological signal measuring device 4 may be incorporated in the ultrasound image diagnosis apparatus 1 as part of its functions.

The ultrasound image diagnosis apparatus 1 is an example of a medical image diagnosis apparatus that is capable of noninvasively examining the internal structure of a subject, the blood flow state, and the like. The ultrasound image diagnosis apparatus 1 is configured to transmit ultrasound waves toward the inside of a subject from the ultrasound probe 2 having transducers (piezoelectric transducers) at the tip, and receive reflected waves caused by acoustic impedance mismatch inside the subject through the transducers of the ultrasound probe 2. The ultrasound image diagnosis apparatus 1 generates an ultrasound image based on the received signal.

The ultrasound probe 2 is configured to transmit ultrasound waves into the subject through each of the ultrasound transducers to scan a scan area, and receive reflected waves from the subject as echo signals. Examples of the scan include various types of scans such as B mode scan and Doppler mode scan. Besides, examples of the ultrasound probe 2 include a sector scan probe, a linear scan probe, a convex scan probe, and the like, and one of them is arbitrarily selected depending on the site to be diagnosed.

Although the ultrasound image diagnosis apparatus 1 is described as including the ultrasound probe 2 in this embodiment, the ultrasound probe 2 is not an essential constituent element. Therefore, the ultrasound image diagnosis apparatus 1 need not necessarily include the ultrasound probe.

The main body 3 includes a transmitting circuit 31, a receiving circuit 32, a signal processing circuit 33, an image processing circuit 34, a display 35, and an input circuit 36. The transmitting circuit 31 is configured to transmit a drive signal to the ultrasound probe 2. The receiving circuit 32 is configured to receive echo signals from the ultrasound probe 2. The signal processing circuit 33 is configured to process the echo signals. The image processing circuit 34 is configured to generate an ultrasound image. The display 35 is configured to display the ultrasound image and also an electrocardiogram received from the biological signal measuring device 4. The input circuit 36 is configured to receive an input signal as being operated by the user such as an examiner.

The main body 3 further includes a communication control circuit 37 configured to control the exchange of signals with other devices (not illustrated), a memory circuit 38, and a control circuit 39 configured to control each part. These and the above circuits are connected to a bus B and can exchange various signals. A timing detector 5, which is configured to detect R waves based on electrocardiographic (ECG) waveforms received from the biological signal measuring device 4, is also connected to the bus B. The functions of each of the circuits are described below in further detail.

Under the control of the control circuit 39, the transmitting circuit 31 generates a drive signal for causing the ultrasound probe 2 to generate ultrasound waves, i.e., an electric pulse signal (hereinafter referred to as "drive pulse") to be applied to each of the piezoelectric transducers. The transmitting circuit 31 transmits the drive pulse to the ultrasound probe 2. The transmitting circuit 31 includes circuits such as, for example, a reference pulse generating circuit, a delay control circuit, a drive pulse generating circuit, and the like (not illustrated), and those circuits perform the functions mentioned above.

The receiving circuit 32 receives an echo signal, i.e., received signal from the ultrasound probe 2. The receiving circuit 32 performs phasing addition on the received signal, and outputs the resultant signal to the signal processing circuit 33.

The signal processing circuit 33 generates various types of data using the received signal from the ultrasound probe 2 fed by the receiving circuit 32, and outputs the data to the image processing circuit 34 and the control circuit 39. The signal processing circuit 33 includes, for example, a B mode processing circuit (or Bc mode processing circuit), a Doppler mode processing circuit, a color Doppler mode processing circuit, and the like (not illustrated). The B mode processing circuit visualizes amplitude information of the received signal, and generates data based on a B mode signal. The Doppler mode processing circuit extracts Doppler shift frequency component from the received signal, and applies fast Fourier transform (FFT) or the like thereto, thereby generating Doppler signal data of blood flow information. The color Doppler mode processing circuit visualizes the blood flow information based on the received signal, and generates data based on a color Doppler mode signal.

The image processing circuit 34 generates two-dimensional or three-dimensional ultrasound images related to the scan area based on the data supplied from the signal processing circuit 33. For example, the image processing circuit 34 generates volume data related to the scan area from the data supplied. Then, from the volume data generated, the image processing circuit 34 generates data of a two-dimensional ultrasound image by multi-planar reconstruction (MPR) or data of a three-dimensional ultrasound image by volume rendering. The image processing circuit 34 outputs the two-dimensional or three-dimensional ultrasound image to the display 35. Examples of the ultrasound image include a B mode image, a Doppler mode image, a color Doppler mode image, an M mode image, and the like.

The display 35 displays various images such as the ultrasound image generated by the image processing circuit 34 and an operation screen (e.g., graphical user interface (GUI) configured to receive various instructions from the user) under the control of the control circuit 39. The display 35 is also capable of displaying the electrocardiogram of the subject. As the display 35, for example, a liquid crystal display (LCD), an organic electroluminescence (EL) display, or the like can be used.

The input circuit 36 receives various input operations made by the user to provide, for example, an instruction to display an image or switch images, designation of the mode, various settings, and the like. For example, GUI, input devices such as buttons, a keyboard, a trackball, a touch panel displayed on the display 35, or the like can be used as the input circuit 36.

Incidentally, in the embodiment, the display 35 and the input circuit 36 are each described as one constituent element of the ultrasound image diagnosis apparatus 1 as illustrated in FIG. 1; however, it is not so limited. For example, the display 35 need not necessarily be a constituent element of the ultrasound image diagnosis apparatus 1, but may be provided separately therefrom. Further, the input circuit 36 may be a touch panel displayed on a separate display.

The communication control circuit 37 enables the ultrasound image diagnosis apparatus 1 to communicate with, for example, medical image diagnosis apparatuses (modalities), servers, medical image processing apparatuses, and the like (not illustrated) each connected to a communication network (not illustrated). Information and medical images exchanged between the communication control circuit 37 and other devices via the communication network may be in conformity with any standard such as digital imaging and communication in medicine (DICOM) or the like. The connection to the communication network or the like may be either wired or wireless.

The memory circuit 38 is formed of, for example, a semiconductor or a magnetic disk. The memory circuit 38 stores programs to be executed by the control circuit 39 and data.

The control circuit 39 comprehensively controls each part of the ultrasound image diagnosis apparatus 1. The control circuit 39 causes the display 35 to display the ultrasound image generated by the image processing circuit 34. Besides, the control circuit 39 controls the timing detector 5 to detect R waves based on ECG waveforms received from the biological signal measuring device 4.

The biological signal measuring device 4 has the function of measuring the ECG waveform of a subject H indicated by a broken line in FIG. 1. The timing detector 5 detects R waves based on the subject H and the ECG waveform received from the biological signal measuring device 4. The internal configurations of the biological signal measuring device 4 and the timing detector 5 are illustrated in FIG. 2.

Figure 2:
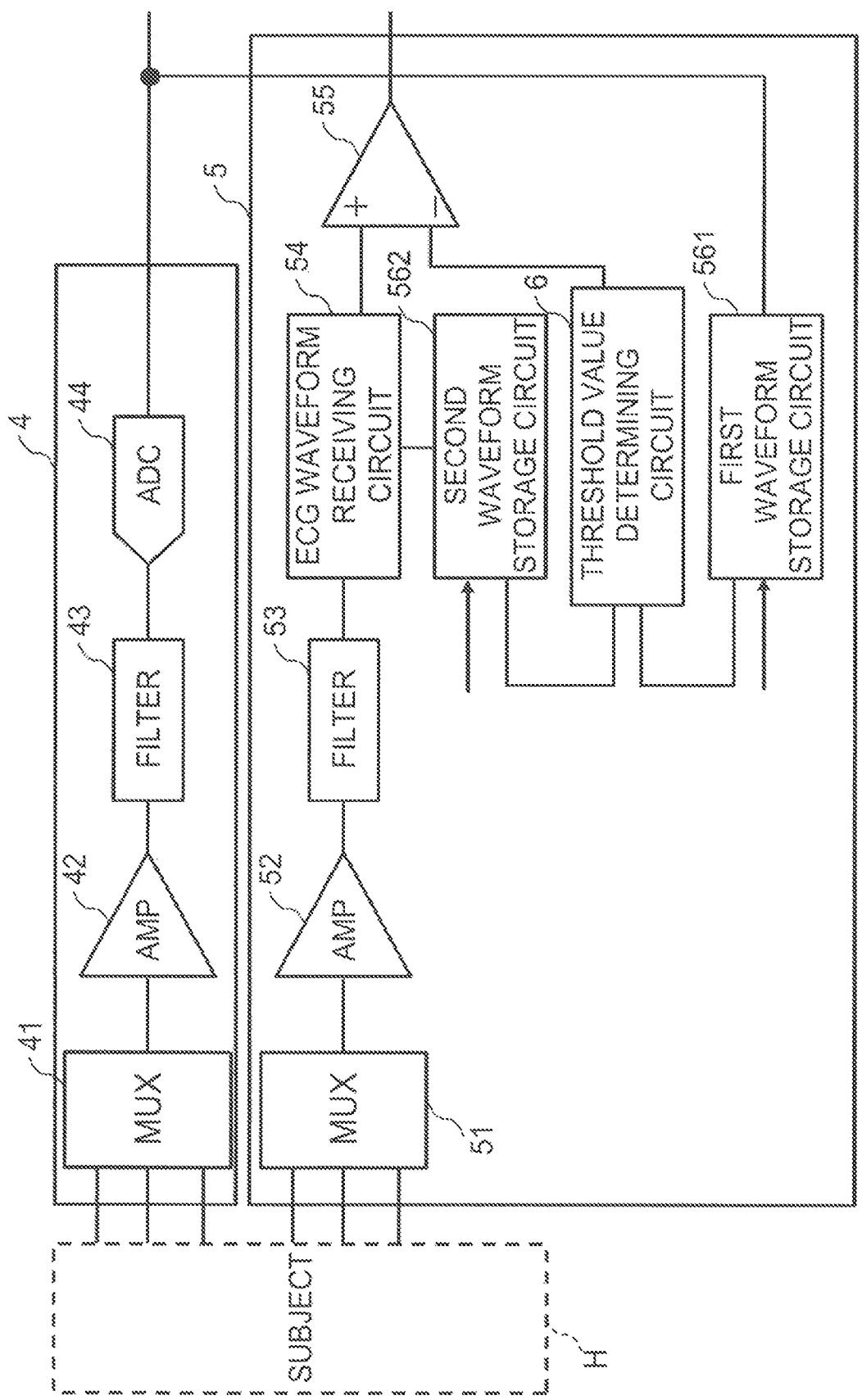
FIG. 2 is a functional block diagram illustrating the internal configuration of each of a biological signal measuring device and a timing detector according to the embodiment.

FIG. 2 is a functional block diagram illustrating the internal configuration of each of the biological signal measuring device 4 and the timing detector 5 according to the embodiment. The biological signal measuring device 4 includes measuring electrodes (not illustrated in FIG. 2), a multiplexer 41, an amplifier circuit 42, a filter 43, and an analog-to-digital (A/D) converter 44.

The measurement electrodes are placed on the body surface of the subject H to detect the ECG waveform. In the example of FIG. 2, three measurement electrodes are placed on the subject H; however, the number of measurement electrodes placed on the subject H is not particularly limited.

ECG waveforms measured at three positions of the subject H are sent from the measuring electrodes to the multiplexer 41. Having received a plurality of signals, the multiplexer 41 outputs them as one signal. In FIG. 2, the multiplexer 41 is indicated as "MUX".

The amplifier circuit 42 amplifies the ECG waveform output from the multiplexer 41 to a predetermined amplitude. In FIG. 2, the amplifier circuit 42 is indicated as "AMP". The filter 43 is set to emphasize R waves in all the waves present in the ECG waveform. The A/D converter 44 converts the ECG waveform, which has passed through the filter 43, into a digital signal. The A/D converter 44 is indicated as "ADC" in FIG. 2.

The ECG waveform output from the A/D converter 44 is input to the display 35. Having received the ECG waveform (electrocardiogram) from the biological signal measuring device 4, the display 35 displays it under the control of the control circuit 39. As illustrated in FIG. 2, the ECG waveform output from the A/D converter 44 is also input to the timing detector 5.

The timing detector 5 is configured to detect an R wave as a trigger for determining the time phase of the heart from the ECG waveform. As can be seen in the overall configuration illustrated in FIG. 1, the timing detector 5 is connected to the subject H and the biological signal measuring device 4. Specifically, as illustrated in FIG. 2, the timing detector 5 receives ECG waveforms from the subject H, and also the ECG waveform sent from the biological signal measuring device 4 to the display 35.

The timing detector 5 includes measurement electrodes (not illustrated in FIG. 2). The timing detector 5 also includes a multiplexer 51, an amplifier circuit 52, a filter 53, an ECG waveform receiving circuit 54, and a comparator 55 on a path of signals sent from the measurement electrodes. The timing detector 5 further includes a first waveform storage circuit 561 which is fed with the ECG waveform output from the A/D converter 44, a second waveform storage circuit 562 which is fed with an ECG waveform output from the ECG waveform receiving circuit 54, and a threshold value determining circuit 6 which is fed with the ECG waveform from each of the first waveform storage circuit 561 and the second waveform storage circuit 562 on a path of a determined threshold value for R wave detection trigger sent to the comparator 55. The threshold value for R wave detection trigger output from the threshold value determining circuit 6 is input to the comparator 55.

The measurement electrodes are placed on the body surface of the subject H to detect the ECG waveform. Although three measurement electrodes are placed on the subject H in the example of FIG. 2, the number of measurement electrodes placed on the subject H is not particularly limited as described above.

In FIG. 2, the measurement electrodes of the biological signal measuring device 4 and those of the timing detector 5 are separately placed on the subject H, and the biological signal measuring device 4 and the timing detector 5 separately acquire ECG waveforms. However, this is just for the sake of convenience of illustration. It suffices if the biological signal measuring device 4 and the timing detector 5 can perform processing on the same ECG waveforms received from the subject H.

ECG waveforms measured at three positions of the subject H are sent from the measuring electrodes to the multiplexer 51. Having received a plurality of signals, the multiplexer 51 outputs them as one signal. In FIG. 2, the multiplexer 51 is indicated as "MUX".

Figure 3:
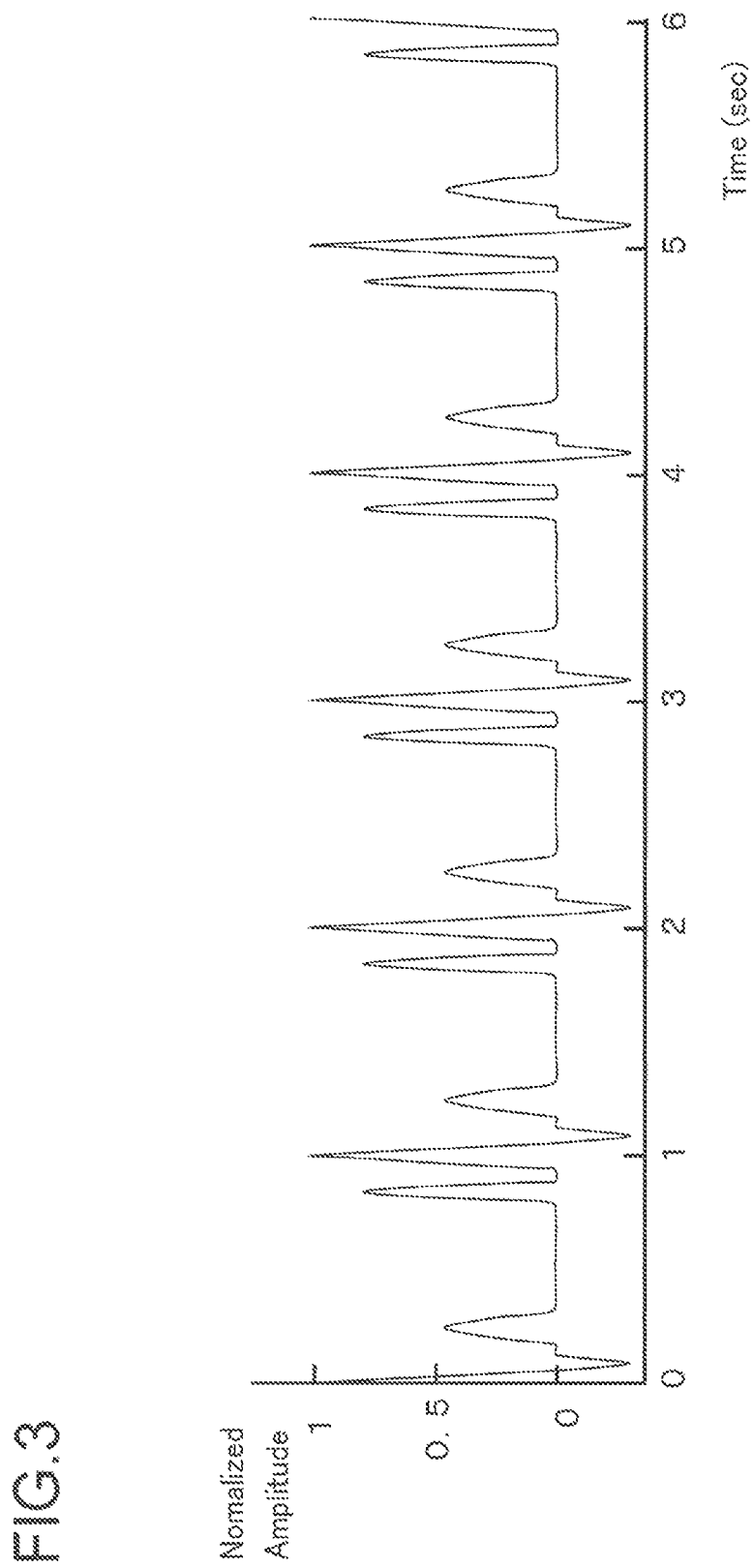
FIG. 3 is a waveform chart illustrating waveforms output from a filter in the biological signal measuring device and the timing detector of the embodiment.

The amplifier circuit 52 amplifies the ECG waveform output from the multiplexer 51 to a predetermined amplitude. In FIG. 2, the amplifier circuit 52 is indicated as "AMP". The filter 53 is set to emphasize R waves in all the waves present in the ECG waveform. FIG. 3 is a waveform chart illustrating waveforms output from the filter 53 in the timing detector 5 of the embodiment.

In the waveform chart of FIG. 3, the vertical axis represents the normalized amplitude, and the horizontal axis represents the time (sec). The waveform chart illustrates five ECG waveforms each consisting of five waves: P wave, Q wave, R wave, S wave, and T wave. There is no characteristic wave in the five ECG waveforms, and it can be said that the ECG waveforms are quite normal.

The R wave is the highest peak in each of the ECG waveforms. As described above, the timing detector 5 detects R waves to detect the interval between two adjacent R waves as one heartbeat.

Incidentally, ECG waveforms output from the biological signal measuring device 4 can be illustrated similarly to the waveform chart illustrated in FIG. 3. Hereinafter, the ECG waveform output from the biological signal measuring device 4 and the waveform output from the filter 53 of the timing detector 5 illustrated in the waveform chart of FIG. 3 are referred to as "first waveform" as appropriate.

The ECG waveform receiving circuit 54 is a so-called full-wave rectifier circuit, and outputs the absolute value of the ECG waveform received.

Figure 4:
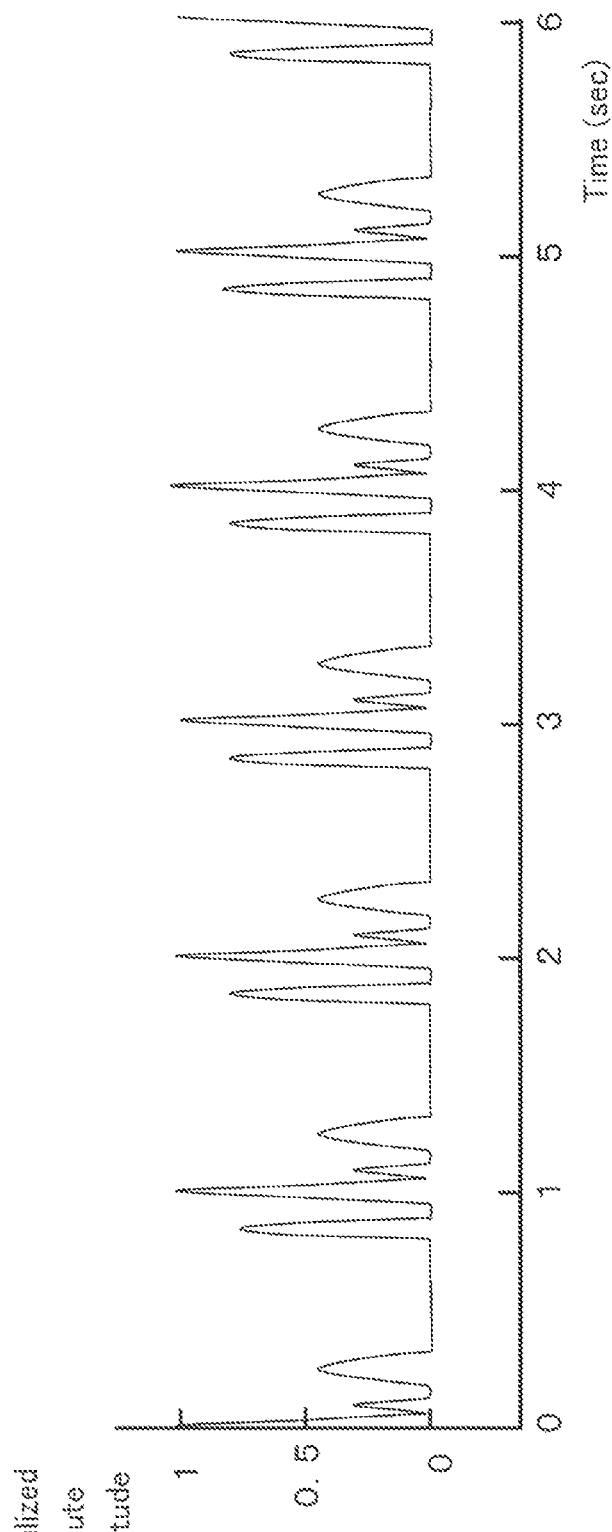
FIG. 4 is a waveform chart illustrating waveforms output from an ECG receiver in the timing detector of the embodiment.

FIG. 4 is a waveform chart illustrating waveforms output from the ECG waveform receiving circuit 54 in the timing detector 5 of the embodiment. In the waveform chart of FIG. 4, the vertical axis represents the amplitude indicated by the normalized absolute value (normalized absolute amplitude), and the horizontal axis represents the time (sec). Having passed through the ECG waveform receiving circuit 54, the ECG waveform is full-wave rectified into a waveform as illustrated in the waveform chart of FIG. 4.

Figure 5:
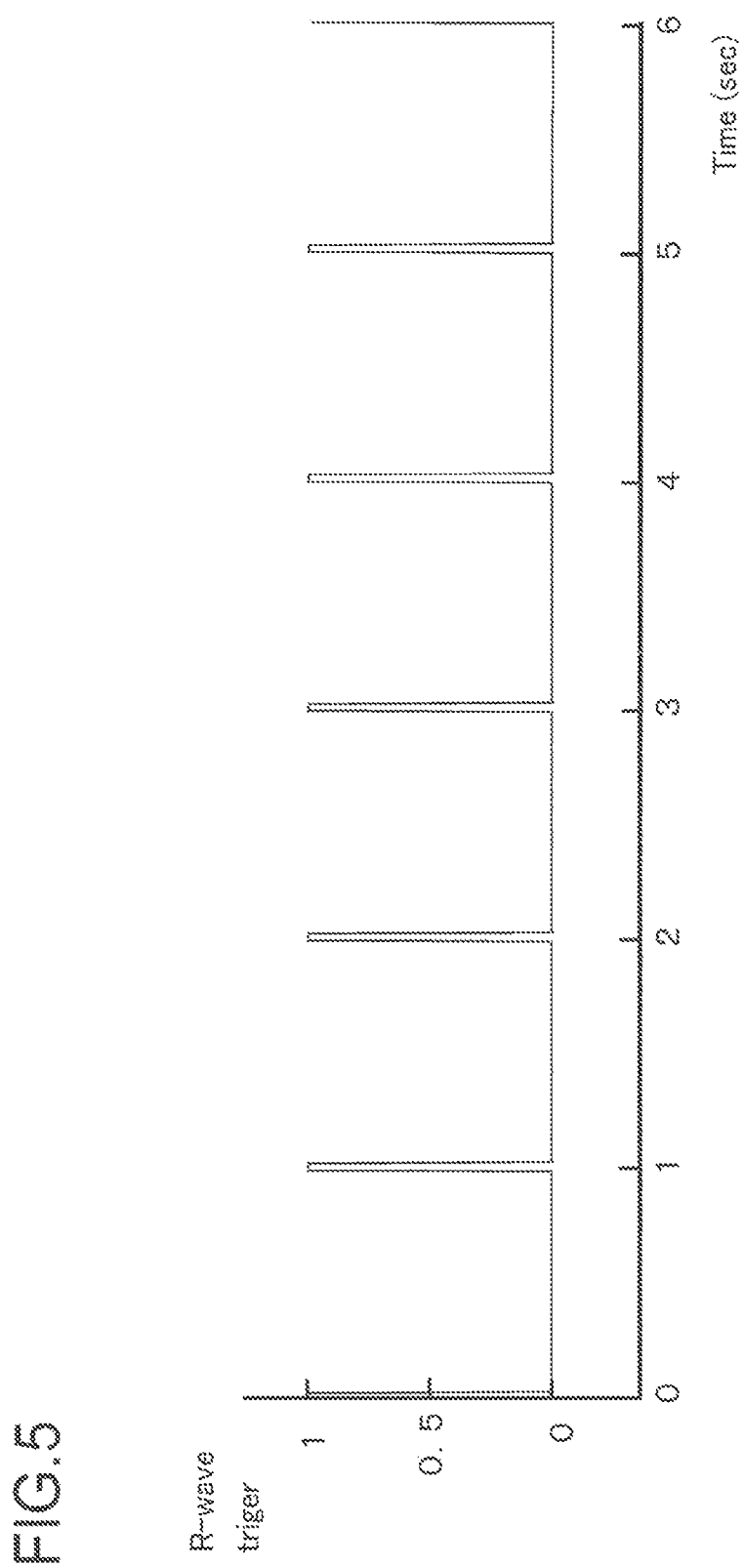
FIG. 5 is a waveform chart illustrating waveforms output in the end from the timing detector of the embodiment.

The comparator 55 compares two input signals and outputs the result. One of the input signals is the ECG waveform which has been full-wave rectified in the ECG waveform receiving circuit 54, and the other is the threshold value for R wave detection trigger which is an output signal from the threshold value determining circuit 6. FIG. 5 illustrates an R wave detection trigger output from the comparator 55.

FIG. 5 is a waveform chart illustrating waveforms output in the end from the timing detector 5 of the embodiment. In the waveform chart of FIG. 5, the vertical axis represents the R wave trigger, and the horizontal axis represents the time (sec). The waveform chart of FIG. 5 illustrates the waveform used as an R wave detection trigger output from the comparator 55.

The waveform output from the ECG waveform receiving circuit 54 illustrated in FIG. 4 is hereinafter referred to as "second waveform" as appropriate. Besides, the waveform used as an R wave detection trigger output from the comparator 55 illustrated in FIG. 5 is hereinafter referred to as "third waveform" as appropriate.

As described above, the ECG waveform output from the biological signal measuring device 4 is sent to the display 35 to be displayed thereon. The ECG waveform is also sent to the timing detector 5. The timing detector 5 determines a final threshold value for R wave detection trigger based on the ECG waveform received from the biological signal measuring device 4.

The first waveform output from the biological signal measuring device 4 is sent to the first waveform storage circuit 561 to be stored therein. The heart rate is calculated in the process of determining the final threshold value for R wave detection trigger. The first waveform stored in the first waveform storage circuit 561 is used for the calculation. Accordingly, the first waveform is sent from the first waveform storage circuit 561 to the threshold value determining circuit 6.

The second waveform output from the ECG waveform receiving circuit 54 is sent to the second waveform storage circuit 562 to be stored therein. The second waveform stored in the second waveform storage circuit 562 is used to set a threshold value used for determining the final threshold value for R wave detection trigger. Accordingly, the second waveform is sent from the second waveform storage circuit 562 to the threshold value determining circuit 6.

Figure 6:
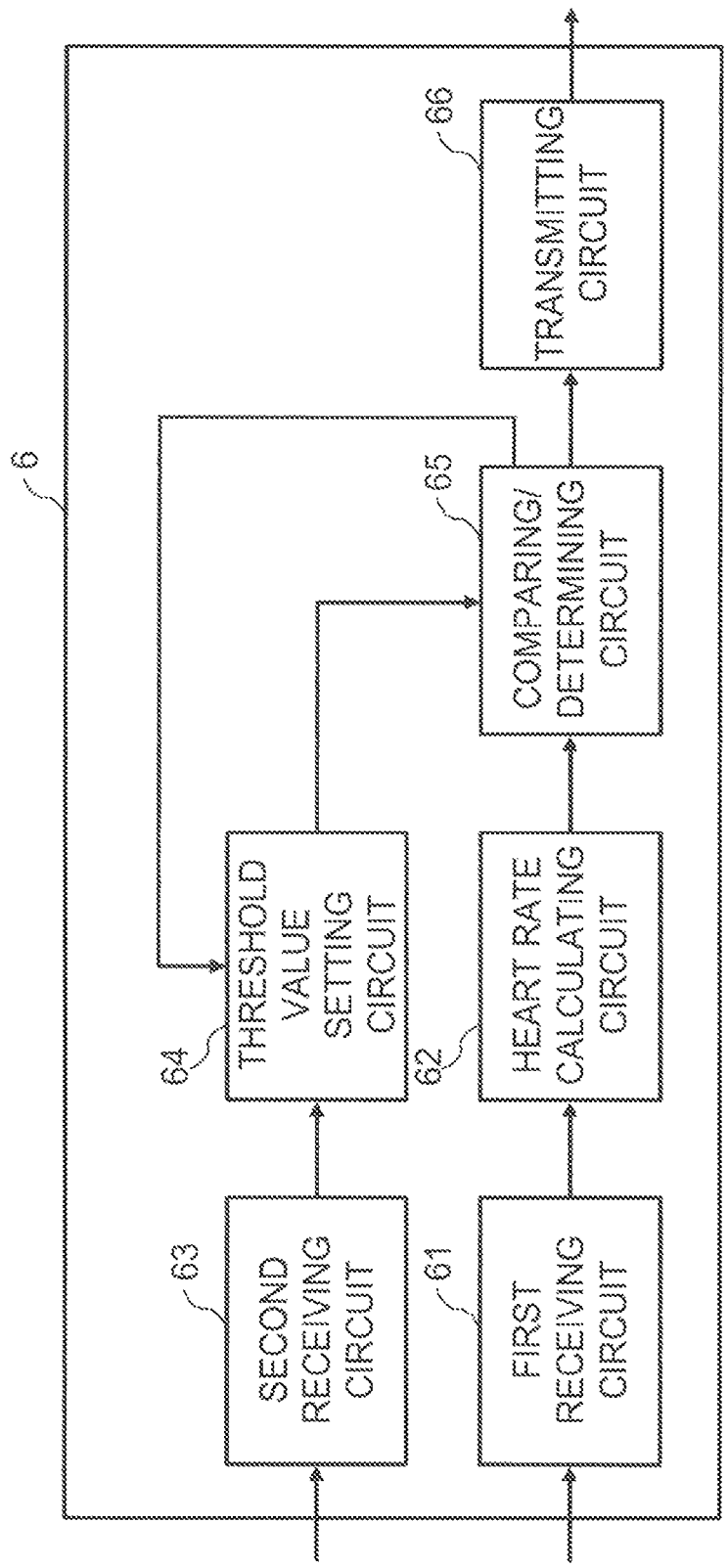
FIG. 6 is a functional block diagram illustrating the internal configuration of a threshold value determining circuit of the embodiment.

The threshold value determining circuit 6 is configured to determine a threshold value for R wave detection trigger for detecting R waves present in the ECG waveform. FIG. 6 is a functional block diagram illustrating the internal configuration of the threshold value determining circuit 6 of the embodiment. The threshold value determining circuit 6 includes a first receiving circuit 61, a heart rate calculating circuit 62, a second receiving circuit 63, a threshold value setting circuit 64, a comparing/determining circuit 65, and a transmitting circuit 66.

The first receiving circuit 61 receives ECG waveforms from the biological signal measuring device 4 via the first waveform storage circuit 561. The heart rate calculating circuit 62 calculates the heart rate based on the ECG waveforms received from the first receiving circuit 61.

The heart rate calculating circuit 62 calculates the heart rate because the heart rate is used for comparison when the comparing/determining circuit 65 determines the threshold value for R wave detection triggering (described later). The heart rate calculating circuit 62 calculates the heart rate based on the ECG waveforms output from the biological signal measuring device 4 and stored in the first waveform storage circuit 561.

Figure 7:
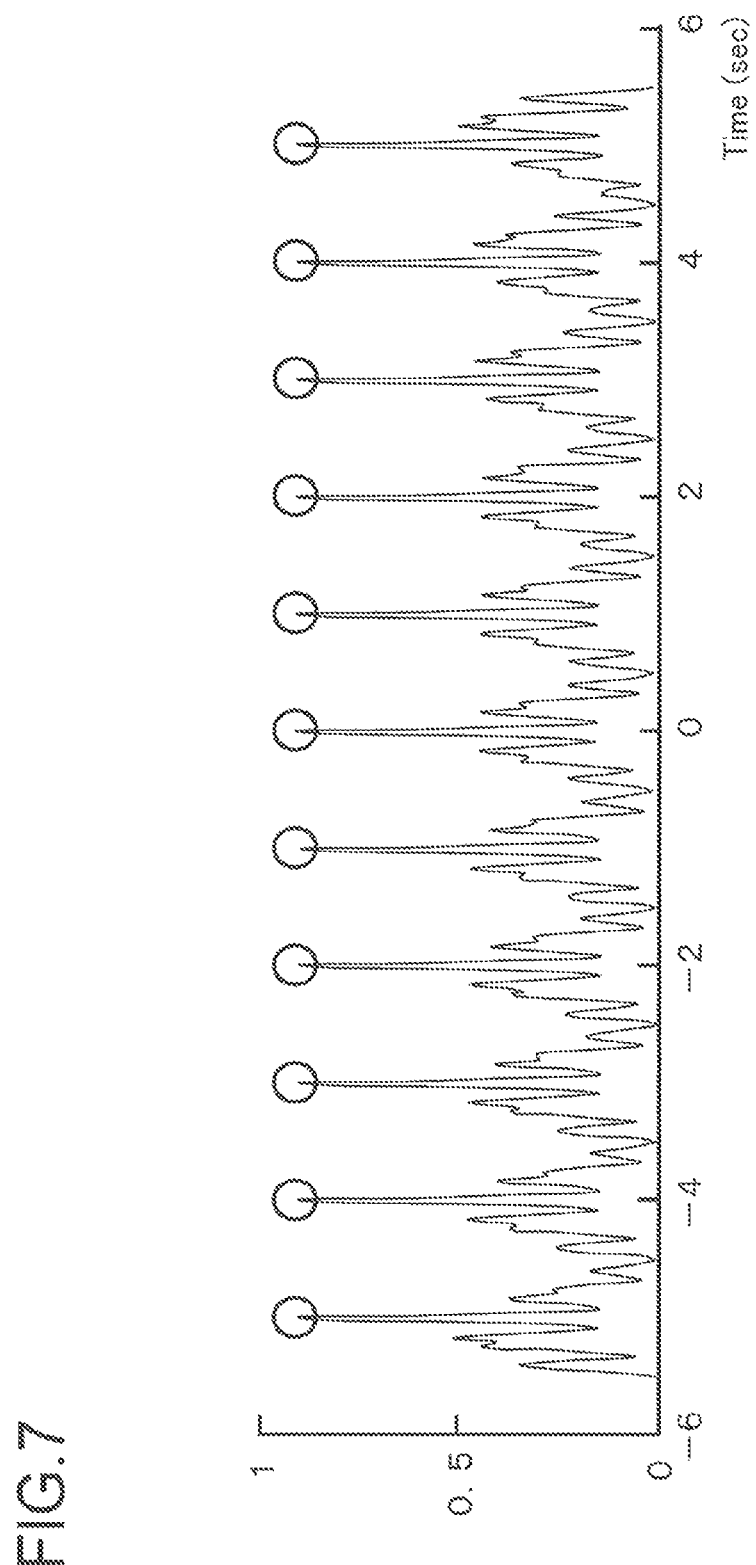
FIG. 7 is an explanatory diagram for explaining the process of calculating the heart rate in the embodiment.

FIG. 7 is an explanatory diagram for explaining the process of calculating the heart rate in the embodiment. The heart rate calculating circuit 62 performs calculation using the autocorrelation to obtain the heart rate from the number of peaks of the waveform. Specifically, referring to the waveform chart of FIG. 7, there are 11 peaks (each surrounded by a circle) in the waveform illustrated in FIG. 7. With this, the heart rate can be calculated as (11+1)/2="6". Hereinafter, the heart rate calculated by the heart rate calculating circuit 62 is referred to as "reference value" as appropriate. This is because the calculated heart rate corresponds to a reference heart rate for determining the threshold value for R wave detection trigger as described above.

The heart rate calculating circuit 62 calculates the heart rate used as a reference value based on, for example, five ECG waveforms most recently stored in the first waveform storage circuit 561 before calculating the heart rate. In other words, the heart rate used as a reference value to determine the threshold value for R wave detection trigger is calculated using five ECG waveforms previous to the one to which the determined threshold value is applied.

That is, for example, upon determining a threshold value for R wave detection trigger to detect the timing of R waves in the ECG waveform of the sixth beat, the heart rate calculating circuit 62 calculates the heart rate using the ECG waveforms of the first to fifth beats. Then, upon determining a threshold value for R wave detection trigger to detect the timing of R waves in the ECG waveform of the seventh beat, the heart rate calculating circuit 62 calculates the heart rate using the ECG waveforms of the second to sixth beats.

In this manner, the heart rate calculating circuit 62 calculates the heart rate while sequentially moving ECG waveforms to be used. That is, when calculating the heart rate used as a reference value, the heart rate calculating circuit 62 uses past (previous) ECG waveforms stored in the first waveform storage circuit 561. The use of past ECG waveforms is intended to increase the accuracy of the threshold value for R wave detection trigger to be determined to thereby increase the precision of R wave detection while fulfilling the demand that R waves as a reference of one heartbeat be detected in real time.

It is not that the heart rate calculating circuit 62 calculates the heart rate only when the first waveform storage circuit 561 stores a plurality of ECG waveforms from the biological signal measuring device 4. It just means that most recent ECG waveforms are used to calculate the heart rate for determining the threshold value for R wave detection trigger at a "certain time point". In other words, it is not that the heart rate is calculated after the first waveform storage circuit 561 is fed with a plurality of ECG waveforms from the biological signal measuring device 4, and then the threshold value for R wave detection trigger is determined.

The threshold value setting circuit 64 sets a threshold value. Specifically, having received an ECG waveform from the ECG waveform receiving circuit 54 via the second waveform storage circuit 562, the second receiving circuit 63 sends the ECG waveform (second waveform) to the threshold value setting circuit 64. As described above, the threshold value setting circuit 64 sets the threshold value based on the second waveform.

In this manner, the threshold value setting circuit 64 sets a threshold value based on the second waveform sent from the second waveform storage circuit 562. This is to adjust the timing with the process performed by the heart rate calculating circuit 62 to set a "reference value" based on the first waveform sent from the first waveform storage circuit 561. Therefore, as in the process of setting the reference value, the threshold value setting circuit 64 sets the threshold value using past (previous) ECG waveforms stored in the second waveform storage circuit 562.

As described above, the heart rate calculating circuit 62 outputs the reference value to the comparing/determining circuit 65. Further, the threshold value setting circuit 64 outputs the threshold value to the comparing/determining circuit 65. The comparing/determining circuit compares the calculated heart rate (reference value) with the number of R wave detection triggers detected using the set threshold value, and determines whether they match.

Although details are described later, there are a range of threshold values at which the number of R wave detection triggers matches the reference value. Accordingly, the comparing/determining circuit 65 determines that the number of R wave detection triggers matches the reference value between the lower limit threshold value (hereinafter referred to as "lower limit value" as appropriate) and the upper limit threshold value (hereinafter referred to as "upper limit value" as appropriate) at which the number of R wave detection triggers matches the reference value.

Since there are a range of threshold values as described above, the comparing/determining circuit 65 needs to determine a threshold value for R wave detection trigger suitable for the comparator 55 to output an R wave detection trigger. The comparing/determining circuit 65 determines a threshold value for R wave detection trigger based on the upper limit value and the lower limit value, and outputs it to the comparator 55 via the transmitting circuit 66.

On the other hand, when the number of R wave detection triggers does not match the reference value, the comparing/determining circuit 65 sends a signal indicating the mismatch to the threshold value setting circuit 64. Having received the signal from the comparing/determining circuit 65, the threshold value setting circuit 64 sends a new threshold value to the comparing/determining circuit 65.

Although the comparing/determining circuit 65 seems to serve a similar role as the comparator 55, their roles are different. That is, the comparing/determining circuit 65 has a function of comparing the number of R wave detection triggers with the reference value detected using the set threshold value. The threshold value output from the comparing/determining circuit 65 via the transmitting circuit 66 is a threshold value for R wave detection trigger determined so that the number of R wave detection triggers matches the reference value. Meanwhile, the comparator 55 is fed with the waveform output from the ECG waveform receiving circuit 54 and the threshold value for R wave detection trigger output from the threshold value determining circuit 6 and compares them. As a result, the comparator 55 outputs the R wave detection trigger as illustrated in FIG. 5.

Next, a detailed description is given of the processing function of the heart rate calculating circuit 62, the threshold value setting circuit 64, and the comparing/determining circuit 65 to determine the threshold value to be output to the comparator 55.

As described above, the comparing/determining circuit 65 compares the calculated heart rate (reference value) with the number of R wave detection triggers detected using the set threshold value, and determines whether they match. Specifically, the determination process proceeds as follows. First, when the heart rate (reference value) is obtained by the heart rate calculating circuit 62, the comparing/determining circuit 65 stores the reference value received from the heart rate calculating circuit 62.

Then, the threshold value setting circuit 64 sets a threshold value. The threshold value setting circuit 64 sets a threshold necessary for the determination process in cooperation with the comparing/determining circuit 65 until the comparing/determining circuit 65 determines a final threshold value for R wave detection trigger to be output to the comparator 55.

Accordingly, at the start of the process of determining a threshold value for R wave detection trigger, the threshold value setting circuit 64 sets an initial threshold value. The threshold value setting circuit 64 sets the initial threshold value based on a signals received from the ECG waveform receiving circuit 54 and the second waveform storage circuit 562. Therefore, the threshold value set here by the threshold value setting circuit 64 is not a threshold value that reflects the result determined by the comparing/determining circuit 65.

Note that since this threshold value is used to detect R waves, a value that can detect all of various waves present in the ECG waveform such as P waves, R waves, T waves is not appropriate. Therefore, a value at which P waves and the R waves are detected is set as the initial threshold value.

Figure 8:
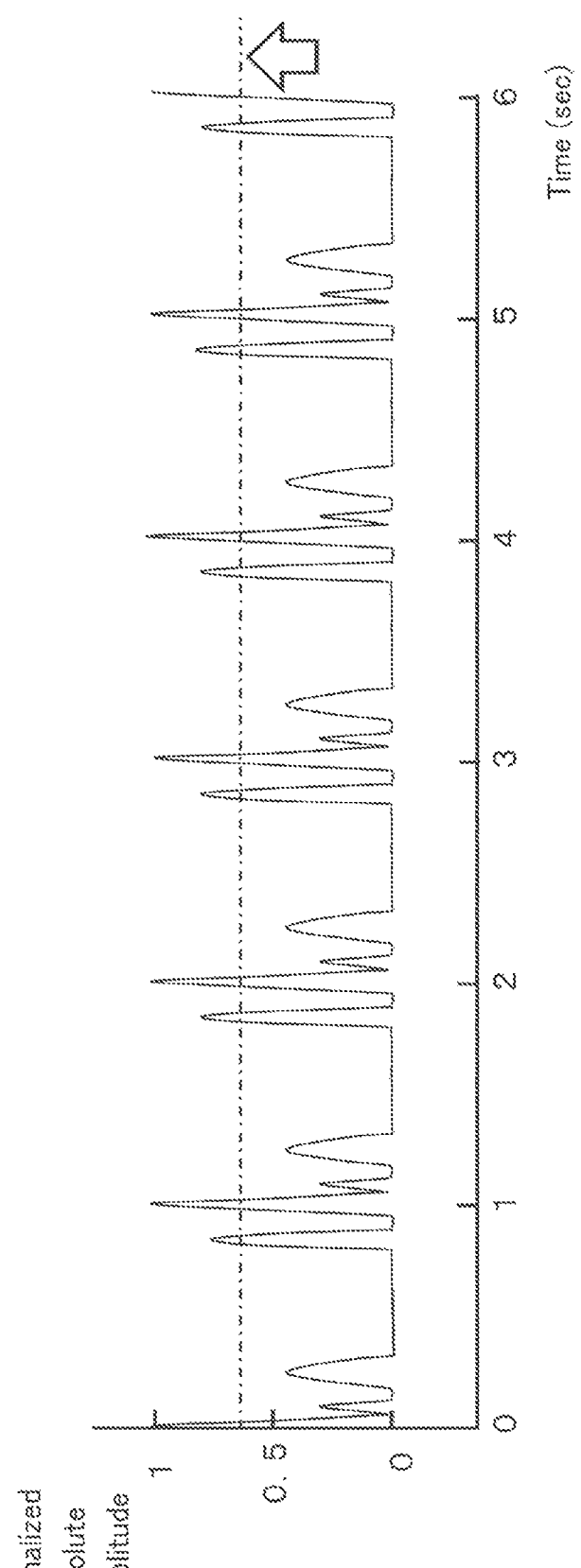
FIG. 8 is an example of a waveform chart for explaining the process of determining a threshold value in the embodiment.

FIG. 8 is an example of a waveform chart for explaining the process of determining a threshold value for R-wave detection trigger in the embodiment. FIGS. 8 to 12 illustrate the waveform (second waveform) output from the ECG waveform receiving circuit 54. In the waveform charts of FIGS. 8 to 12, the vertical axis represents the amplitude indicated by the normalized absolute value (normalized absolute amplitude), and the horizontal axis represents the time (sec). In FIG. 8, R waves have the highest amplitude, and P waves, each occurring before an R wave, have the next highest amplitude.

In FIG. 8, the threshold value set as the initial value by the threshold value setting circuit 64 is indicated by a one-dot chain line. As described above, it suffices if the threshold value is set within a range necessary for detecting R waves. In the example of FIG. 8, the initial value is set to around where the amplitude exceeds 0.5. Then, the threshold value is increased as indicated by a large arrow in FIG. 8 to figure out the upper limit and lower limit of the threshold value at which the number of R wave detection triggers matches the reference value. Setting of such an initial value can prevent the detection of other waves than P waves and R waves such as, for example, T waves.

The initial threshold value set by the threshold value setting circuit 64 is sent to the comparing/determining circuit 65. Thus, the comparing/determining circuit 65 receives the reference value from the heart rate calculating circuit 62 and the threshold value from the threshold value setting circuit 64. In the following, an example is described in which the heart rate calculating circuit 62 obtains "6" as the heart rate based on the waveform illustrated in FIG. 7.

As described above, the initial threshold value is indicated by a one-dot chain line in FIG. 8. With reference to the initial threshold value, there are "12" peaks in the waveform. The comparing/determining circuit 65 counts the number of peaks using the set threshold value. The number of peaks thus counted using the set threshold value corresponds to the number of R wave detection triggers.

In the waveform chart of FIG. 8, it is understood that the number of peaks counted using the set threshold value includes P waves as well as R waves. However, the comparing/determining circuit 65 does not count the number of peaks while regarding each of them as an R wave or a P wave. Therefore, the number of peaks including P waves is herein referred to as "the number of R wave detection triggers".

The comparing/determining circuit 65 compares the number of R wave detection triggers "12" with the reference value "6". In this case, the number of R wave detection triggers (12) does not match the reference value (6), and it means that other waves than R waves have also been detected. Accordingly, the comparing/determining circuit 65 instructs the threshold value setting circuit 64 to set a threshold value again.

According to the instruction from the comparing/determining circuit 65, the threshold value setting circuit 64 changes the threshold value set as the initial value to set another threshold value. In this case, the amplitude set as the threshold value is increased to set a new threshold value.

Then, the threshold value setting circuit 64 sends the new threshold value to the comparing/determining circuit 65. The comparing/determining circuit 65 compares the new threshold value with the reference value, and determines whether the number of R wave detection triggers matches the reference value.

Having determined that the number of R wave detection triggers does not match the reference value, the comparing/determining circuit instructs the threshold value setting circuit 64 to set a new threshold value as described above. At this time, the comparing/determining circuit 65 may also instruct the threshold value setting circuit 64 as to how much the amplitude indicated by the threshold value needs to be increased. This process is repeated until the number of R wave detection triggers matches the reference value.

Figure 9:
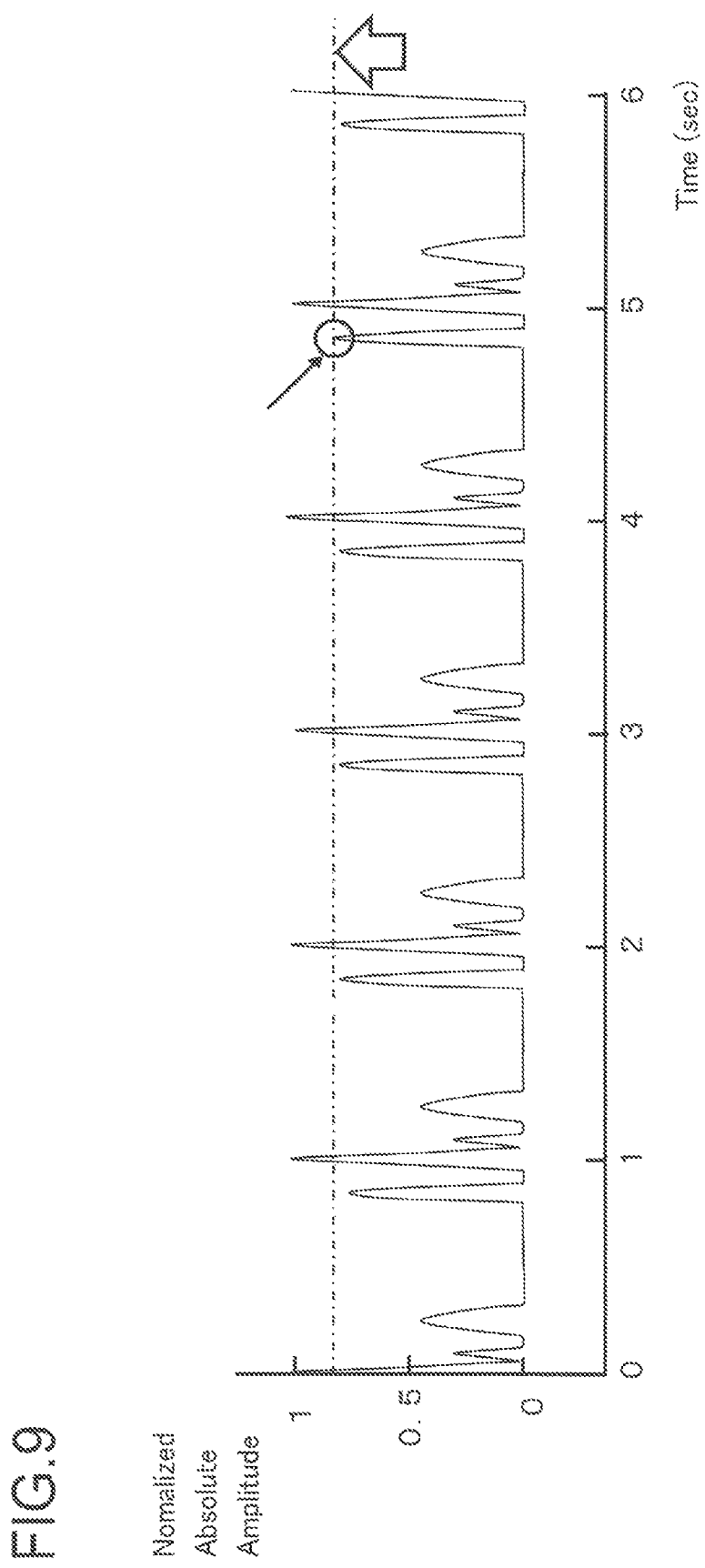
FIG. 9 is another example of a waveform chart for explaining the process of determining a threshold value in the embodiment.

In the waveform chart of FIG. 9, the threshold value is set at the position of the highest peak indicated by a circle and an arrow among those identified as P waves. Since the threshold value is set at the position of the highest P wave, P waves lower than the highest one are present below the threshold value.

In this manner, if the threshold value is set such that only R waves have higher amplitude than the threshold value, the number of peaks that the comparing/determining circuit 65 counts as the number of R wave detection triggers matches the reference value. That is, if the threshold value is set like this, P waves are prevented from being included in R wave detection triggers, and R waves (the same number of R waves as the reference value) can be accurately detected.

In the process of determining the threshold value as described above, the comparing/determining circuit 65 stores a threshold value at which the number of R wave detection triggers matches the reference value first. This threshold value corresponds to the "lower limit value" mentioned above. Then, the comparing/determining circuit 65 instructs the threshold value setting circuit 64 to set a new threshold value. The threshold value setting circuit 64 sets a threshold value according to the instruction, and sends it to the comparing/determining circuit 65.

Figure 10:
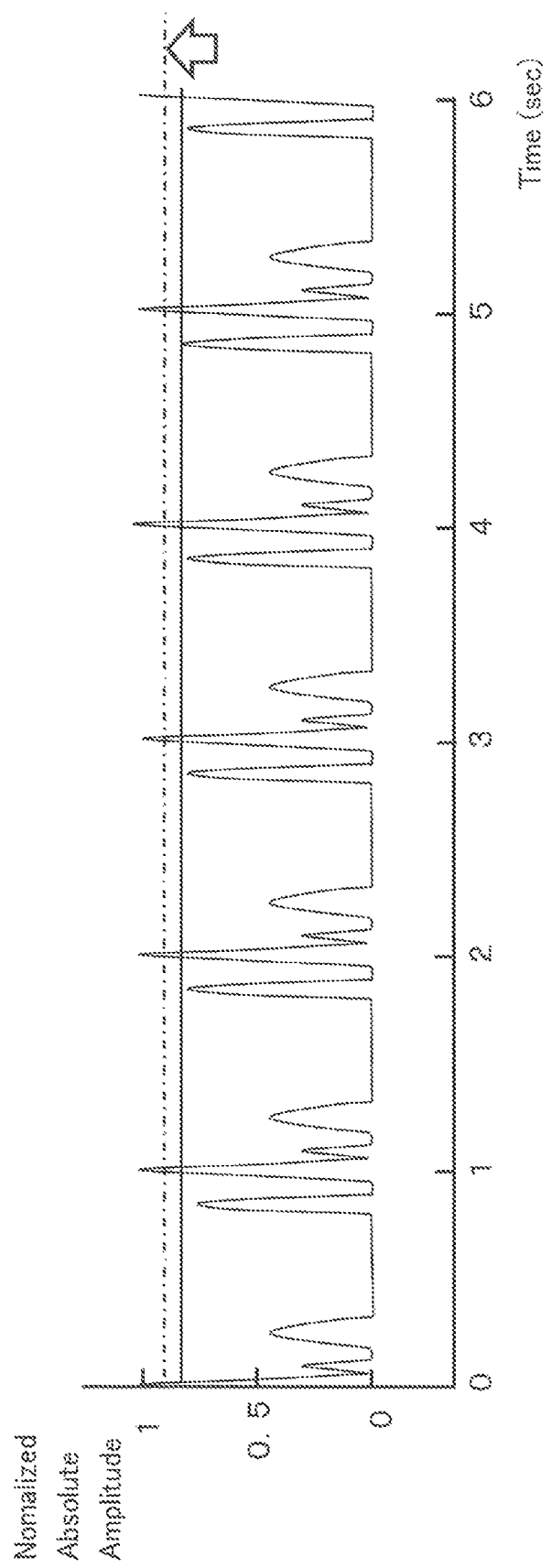
FIG. 10 is another example of a waveform chart for explaining the process of determining a threshold value in the embodiment.

When the comparing/determining circuit 65 compares the number of R wave detection triggers with the reference value using threshold values further set above the lower limit value, the number of R wave detection triggers keeps matching the reference value for a while. FIG. 10 illustrates this state using a waveform chart. In FIG. 10, the set threshold value is indicated by a one-dot chain line, and the lower limit value is indicated by a solid line. The number of R wave detection triggers counted using the threshold value of FIG. 10 is "6", which matches the reference value.

Figure 11:
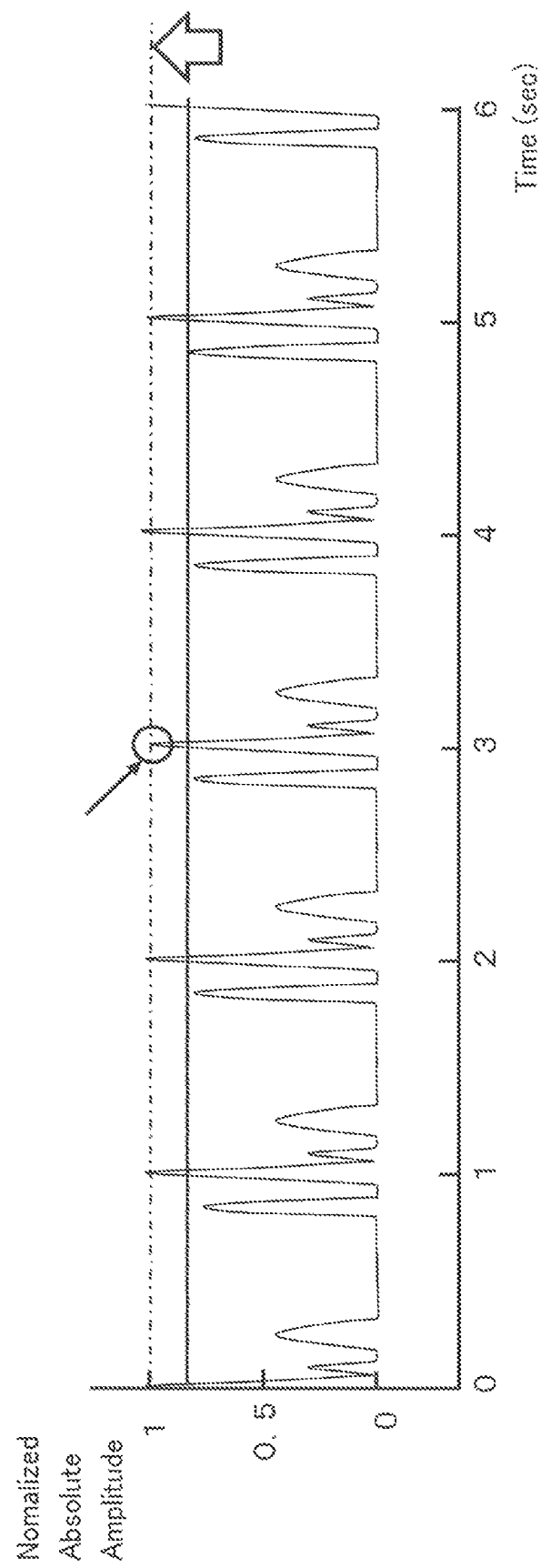
FIG. 11 is another example of a waveform chart for explaining the process of determining a threshold value in the embodiment.

In the process in which the threshold value setting circuit 64 sets a threshold value and sends it to the comparing/determining circuit 65, and the comparing/determining circuit 65 compares the number of R wave detection triggers with the reference value, the threshold value is set at the position of the lowest peak among those identified as R waves in due course. FIG. 11 illustrates this state using a waveform chart.

FIG. 11 illustrates a state where a threshold value is set at the position of the lowest R wave among those having various peak values. The peak of the lowest R wave is indicated by a circle and an arrow. When the threshold value is set to a value higher than this value, the number of peaks counted as the number of R wave detection triggers becomes "5" or less, which does not match the reference value. The comparing/determining circuit 65 stores this threshold value as "upper limit value".

That is, the lower limit of the threshold value corresponds to the peak of the highest P wave acquired so far. This is because if the threshold value is set lower than the peak value, P waves are also detected. On the other hand, the upper limit corresponds to the peak of the lowest R wave acquired so far in a certain cycle. This is because if the threshold value is set higher than the peak value, some of R waves cannot be detected. Such setting the threshold value enables the reliable detection of R waves while preventing P waves from being detected.

Figure 12:
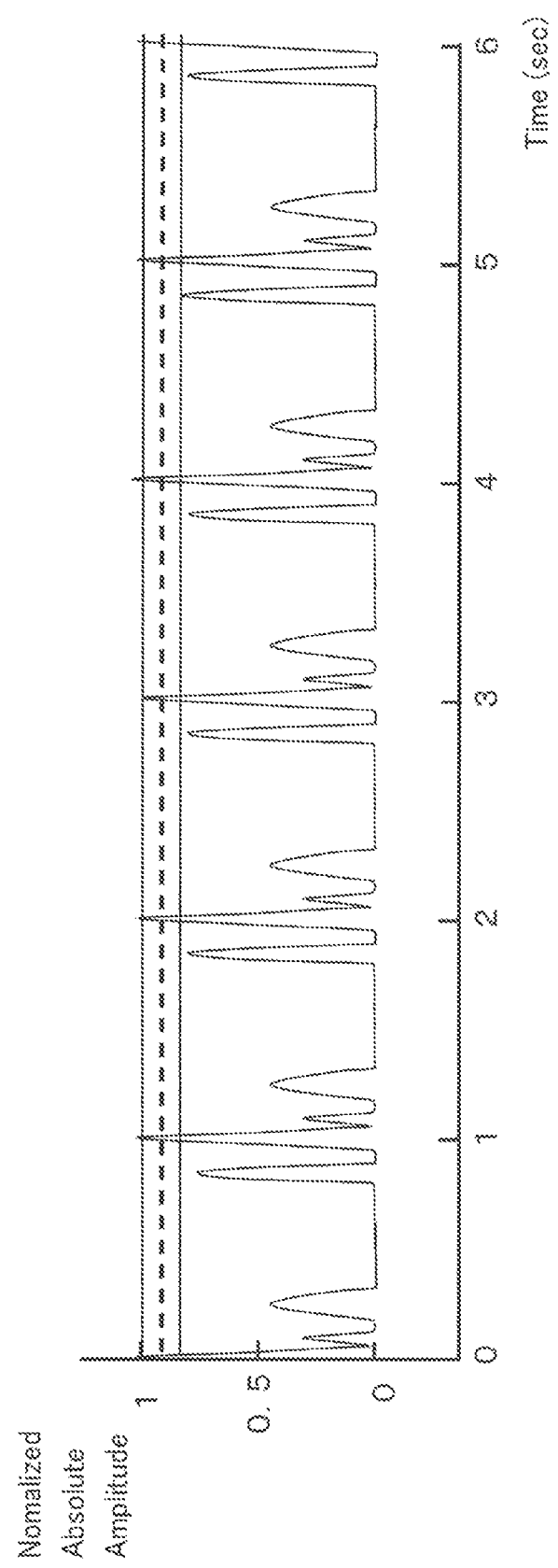
FIG. 12 is another example of a waveform chart for explaining the process of determining a threshold value in the embodiment.

The comparing/determining circuit 65 obtains the upper limit and lower limit of the threshold value at which the number of R wave detection triggers matches the reference value, and determines the midpoint value between them as a threshold value. FIG. 12 illustrates this state using a waveform chart. In FIG. 12, the lower limit value and the upper limit value are indicated by solid lines, and the midpoint value is indicated by a broken line. This threshold value indicated by a broken line is the threshold value for R wave detection trigger determined by the threshold value determining circuit 6. Having determined the threshold value for R wave detection trigger, the threshold value determining circuit 6 sends it to the comparator 55 via the transmitting circuit 66.

In the process of determining the threshold value, the lower limit value and the upper limit value are obtained, and then the midpoint value is determined as the threshold value. However, the threshold value for R wave detection trigger need not always be the midpoint value between the lower limit value and the upper limit value. The threshold value for R wave detection trigger may be determined in an arbitrary manner as long as it is determined so that R waves can be reliably detected by the comparator 55.

Each time having output the determined threshold value for R wave detection trigger to the comparator 55, the threshold value determining circuit 6 is fed with a waveform from the first waveform storage circuit 561 and the second waveform storage circuit 562 (hereinafter collectively referred to as "waveform storage circuit 56" when their functions can be collectively described).

That is, the threshold value determining circuit 6 is not always fed with a waveform from the waveform storage circuit 56, but receives no input therefrom while the comparing/determining circuit 65 is performing the process of comparing the number of R wave detection triggers with the reference value using the set threshold value and determining the threshold value for R wave detection trigger.

The control circuit 39 calculates the reference value, and determines whether to send data required to set a threshold value necessary for detecting the number of R wave detection triggers from the waveform storage circuit 56 to the threshold value determining circuit 6. In FIG. 2, arrows pointing to the first waveform storage circuit 561 and the second waveform storage circuit 562 of the timing detector 5 indicate input of signals from the control circuit 39.

The threshold value for R wave detection trigger to detect R waves in the ECG waveform is described as being determined by the threshold value determining circuit 6; however, it need not necessarily be determined by the threshold value determining circuit 6, but may be determined by the control circuit 39 using, for example, its threshold value determination function.

In this case, the threshold value determination function of the control circuit 39 can be realized by, for example, a computer program that is stored in a predetermined memory, the memory circuit 38, or the like and executed by a processor. The term "processor" as used herein refers to a circuit such as, for example, a dedicated or general central processing unit (CPU) arithmetic circuit (circuitry), an application specific integrated circuit (ASIC), a programmable logic device such as a simple programmable logic device (SPLD) and a complex programmable logic device (CPLD), a field programmable gate array (FPGA), or the like.

The processor reads out, for example, a program stored in the memory circuit 38 or directly incorporated in the circuit of the processor and executes it, thereby realizing the function. Each processor may be provided with a recording circuit for storing the program. The recording circuit may store, for example, a program corresponding to the functions of the signal processing circuit 33 illustrated in FIG. 1, and may have the configuration of the memory circuit 38 illustrated in FIG. 1. The memory circuit is formed of a storage device, examples of which include a semiconductor memory such as a general random access memory (RAM) and a magnetic disk such as a hard disc drive (HDD).

[Operation]

Figure 13:
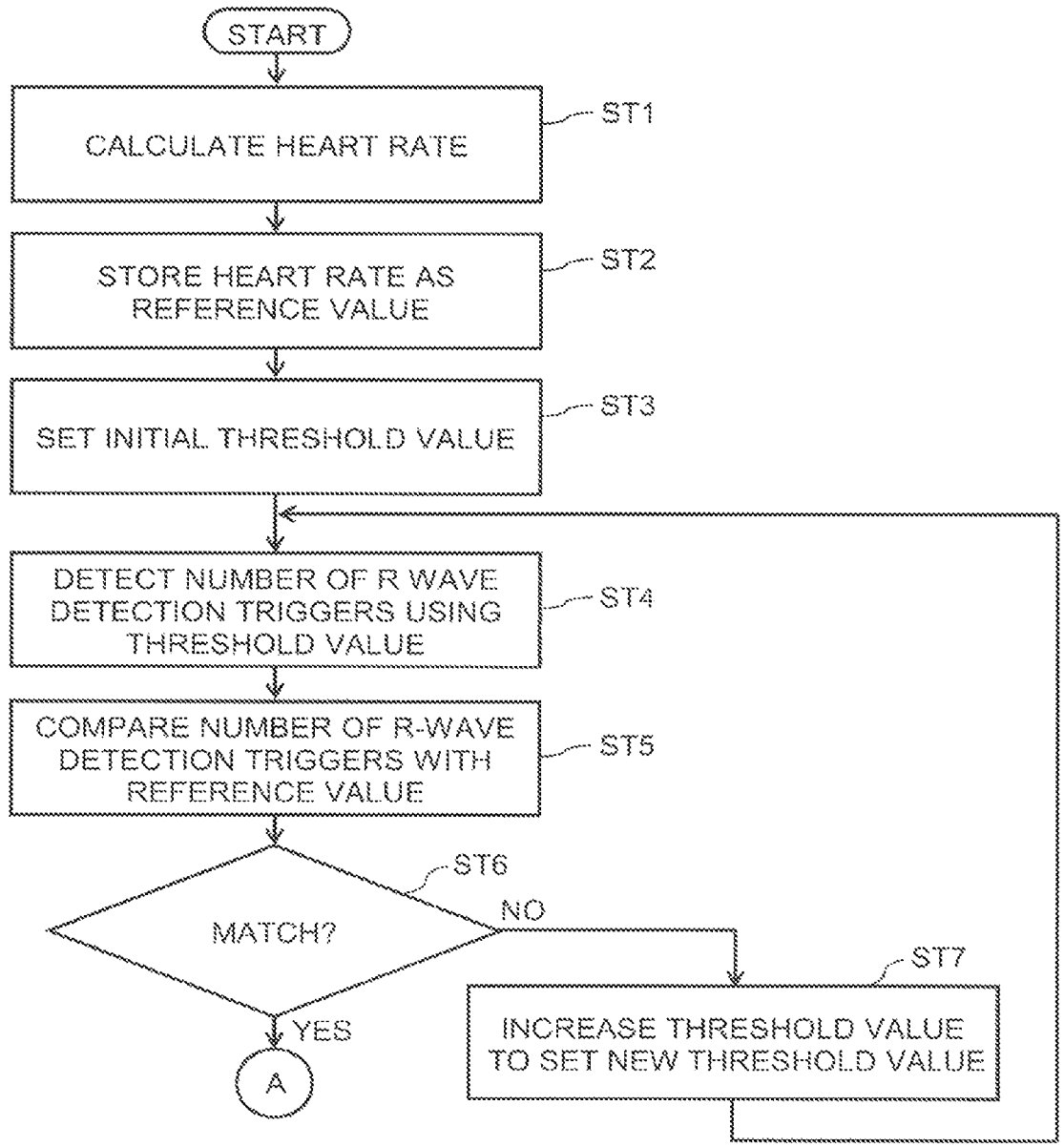
FIG. 13 is a flowchart illustrating the operation of the threshold value determining circuit to determine a threshold value according to the embodiment.
Figure 14:
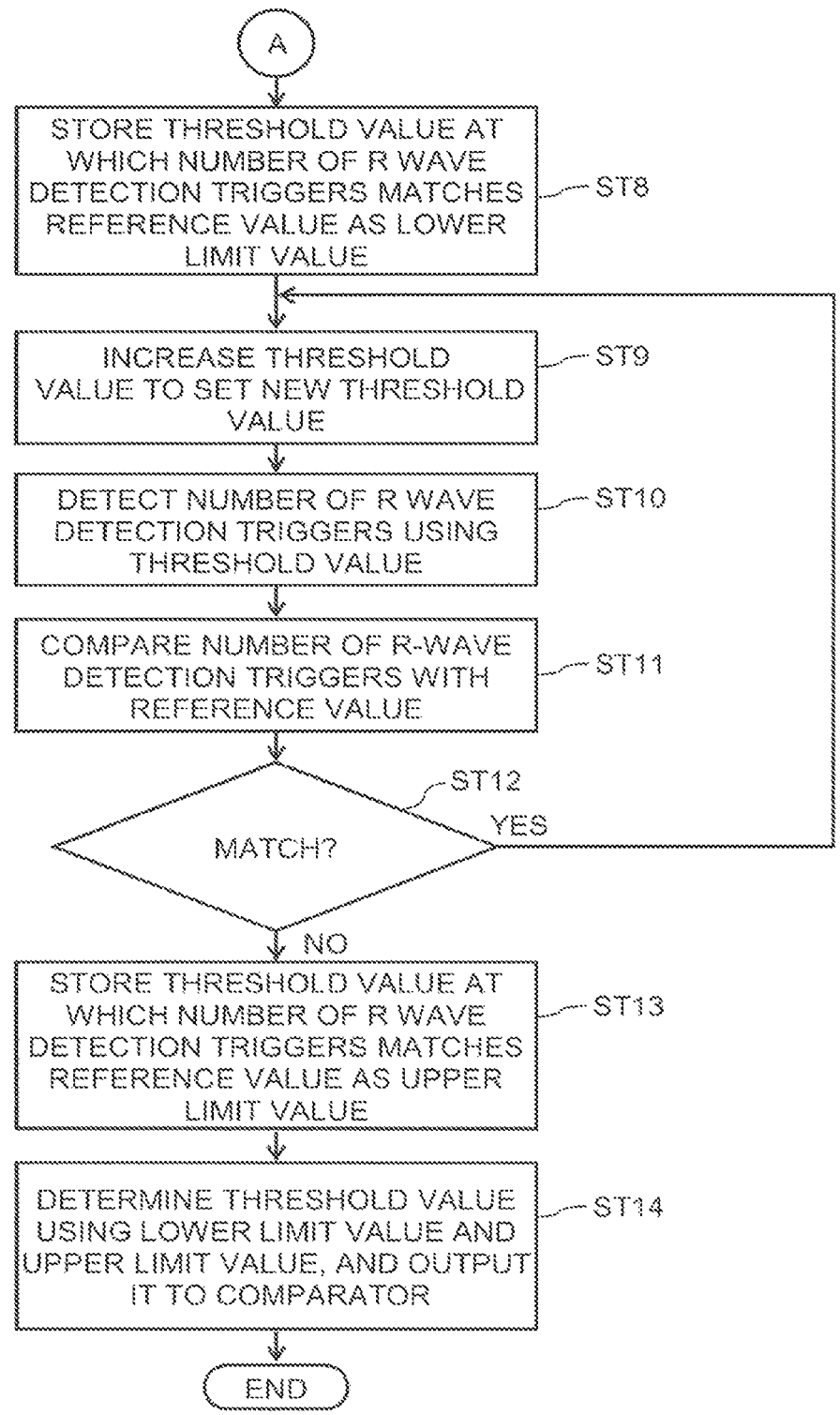
FIG. 14 is a flowchart illustrating the operation of the threshold value determining circuit to determine a threshold value according to the embodiment.

Next, with reference to FIGS. 13 and 14, a description is given of the operation of the threshold value determining circuit 6 to determine a threshold value for R wave detection trigger. FIGS. 13 and 14 are flowcharts illustrating the operation of the threshold value determining circuit 6 to determine a threshold value for R wave detection trigger according to the embodiment. The following process of determining a threshold value is performed for each heartbeat. When a threshold value is determined for one heartbeat, the process is repeated from the beginning.

First, the heart rate calculating circuit 62 calculates the heart rate (ST1). As described above, the heart rate calculating circuit 62 calculates the heart rate based on ECG waveforms output from the biological signal measuring device 4 and stored in the first waveform storage circuit 561. The heart rate calculating circuit 62 sends the obtained heart rate to the comparing/determining circuit 65. The comparing/determining circuit 65 stores the heart rate as a reference value (ST2).

Meanwhile, the threshold value setting circuit 64 sets a threshold value using the second waveform received from the ECG waveform receiving circuit 54 through the second waveform storage circuit 562 (ST3). This threshold value set by the threshold value setting circuit 64 is an initial threshold value.

The comparing/determining circuit 65 detects the number of R wave detection triggers using the threshold value sent from the threshold value setting circuit 64 (ST4). Then, the comparing/determining circuit 65 compares the number of R-wave detection triggers with the stored reference value (ST5).

Having determined that the number of R wave detection triggers does not match the reference value as a result of the comparison (NO in ST6), the comparing/determining circuit 65 instructs the threshold value setting circuit 64 to set a new threshold value. The threshold value setting circuit 64 increases the threshold value to set a new threshold value according to the instruction (ST7).

The threshold value setting circuit 64 sends the new threshold value to the comparing/determining circuit 65. The comparing/determining circuit 65 detects again the number of R wave detection triggers using the new threshold value (ST4), and compares the number of R wave detection triggers with the reference value (ST5). The comparing/determining circuit 65 repeats this process until the number of R wave detection triggers matches the reference value.

Having determined that the number of R wave detection triggers matches the reference value (YES in ST6), the comparing/determining circuit 65 stores the threshold value at which the number of R wave detection triggers matches the reference value as the lower limit value (ST8 in FIG. 14).

Then, the comparing/determining circuit 65 continues the process of determining whether the number of R wave detection triggers matches the reference value. Accordingly, the threshold value setting circuit 64 further increases the threshold value to set a new threshold value (ST9), and sends it to the comparing/determining circuit 65.

The comparing/determining circuit 65 detects the number of R wave detection triggers using the new threshold value (ST10), and compares the number of R wave detection triggers with the reference value (ST11). Having determined that the number of R wave detection triggers matches the reference value as a result of the comparison (YES in ST12), the comparing/determining circuit 65 instructs the threshold value setting circuit 64 to increase the threshold value to set a new threshold value. The threshold value setting circuit 64 sets a new threshold value according to the instruction (ST9 in FIG. 13).

When the number of R wave detection triggers no longer matches the reference value (NO in ST12), the comparing/determining circuit 65 stores the threshold value at which the number of R wave detection triggers matches the reference value as the upper limit value (ST13).

Thereafter, the comparing/determining circuit 65 determines a threshold value for R wave detection trigger using the lower limit value and the upper limit value, and outputs it to the comparator 55 (ST14). With this, the threshold value determining circuit 6 completes the process of determining a threshold value for R wave detection trigger to be used in the comparator 55.

Through the process as described above, it is possible to reliably detect R waves in the ECG waveform used as a trigger for determining the phase of the heart cycle while reducing erroneous detection.

In particular, when the heart rate calculating circuit 62 calculates the heart rate used as a reference value, and also when the threshold value setting circuit 64 sets a threshold value for R wave detection trigger, they use past data stored in the waveform storage circuit 56 immediately before the calculation. Thereby, a highly accurate threshold value for R wave detection trigger can be set taking into account the real time property.

(Modification)

The operation of the threshold value setting circuit 64 to set a threshold value for R wave detection trigger is described above assuming that the same waveform is periodically received from the subject. ECG waveforms output from the biological signal measuring device 4 and the timing detector 5 are intended to display signals received from the subject as an electrocardiogram.

For example, if the subject moves or an irregular heartbeat or the like occurs during measurement, the movement may produce changes in first waveform and second waveform. The use of these waveforms may cause noise, resulting in affecting the determination of the final threshold value for R wave detection trigger. Therefore, in the process of determining a threshold value for R wave detection trigger described below, such a cause of noise is eliminated in advance.

Figure 15:
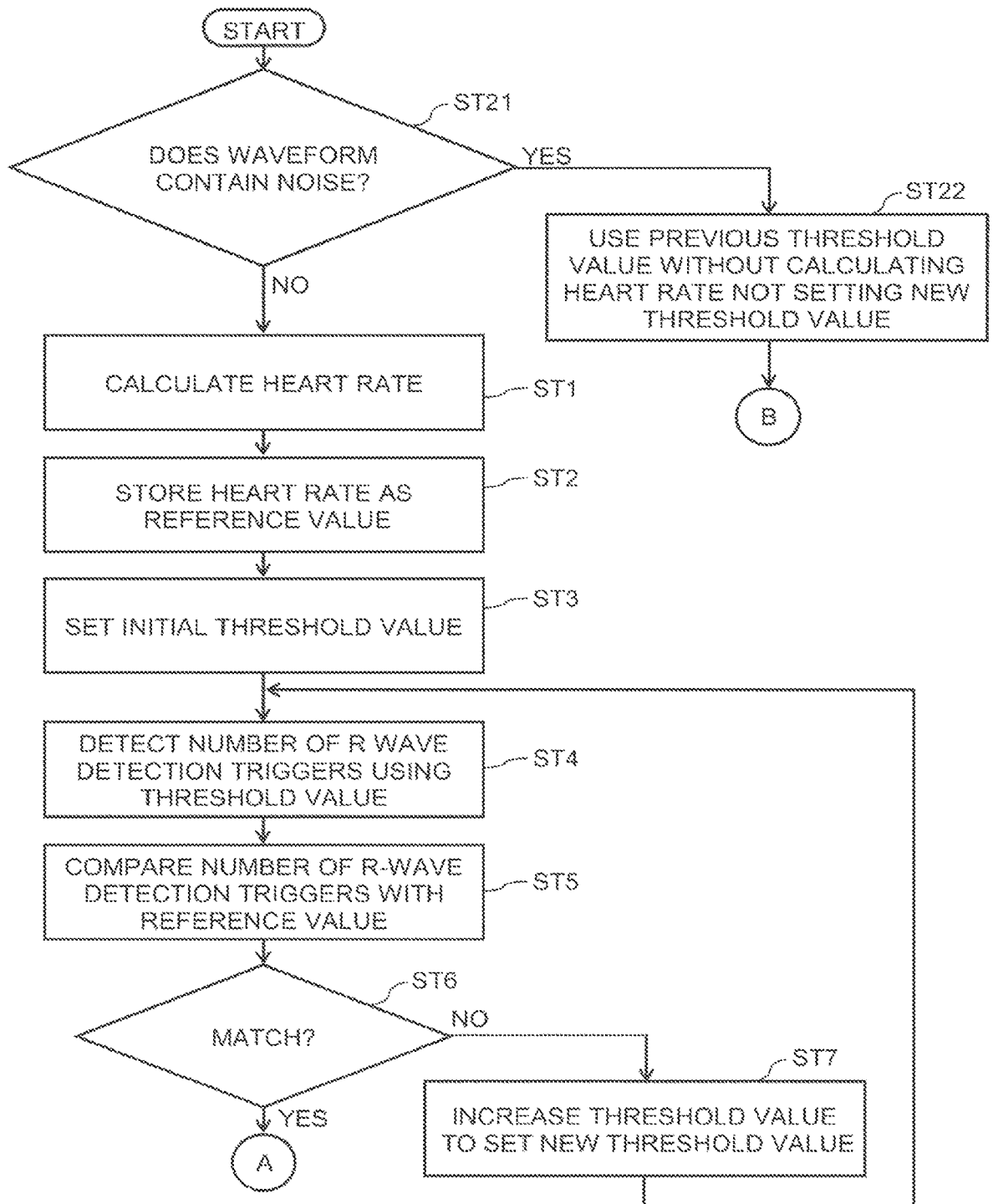
FIG. 15 is a flowchart illustrating the operation of the threshold value determining circuit to determine a threshold value according to a modification of the embodiment.
Figure 16:
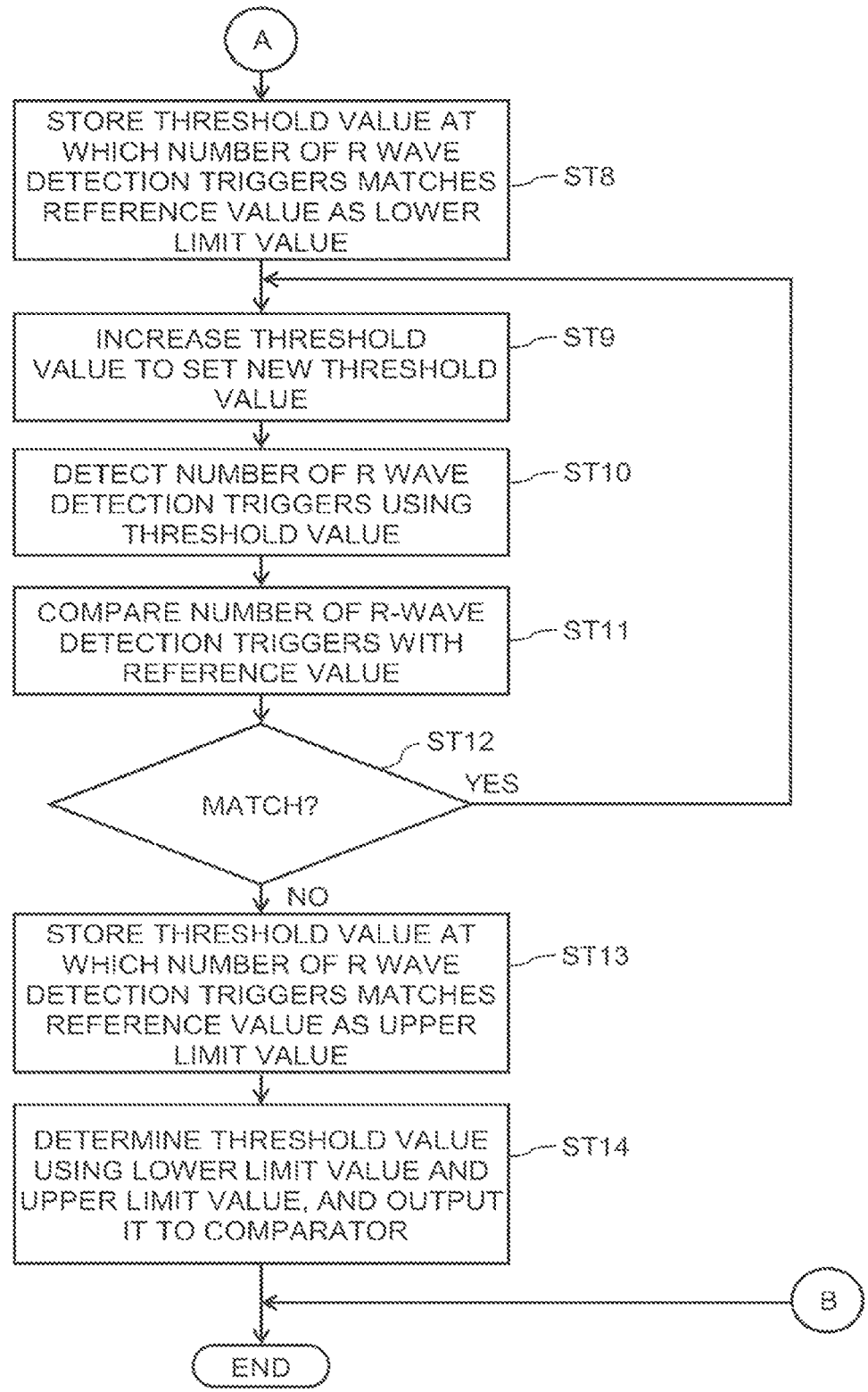
FIG. 16 is a flowchart illustrating the operation of the threshold value determining circuit to determine a threshold value according to a modification of the embodiment.

FIGS. 15 and 16 are flowcharts illustrating the operation of the threshold value determining circuit 6 to determine a threshold value for R wave detection trigger according to a modification of the embodiment. In the modification, the threshold value determining circuit 6 checks whether the waveform contains noise before determining a threshold value for R wave detection trigger (ST21).

Specifically, the heart rate calculating circuit 62 checks whether first waveforms stored in the first waveform storage circuit 561 include an irregular waveform having no periodicity. The term "noise" as used herein refers to a waveform that has no periodicity due to the body movement, irregular heartbeat, or the like of the subject. Besides, the threshold value setting circuit 64 checks whether second waveforms stored in the second waveform storage circuit 562 include an irregular waveform having no periodicity.

Having determined that either or both of the first waveform storage circuit 561 and the second waveform storage circuit 562 store an irregular waveform (YES in ST21), the heart rate calculating circuit 62 does not newly calculate the heart rate, and the threshold value setting circuit 64 does not set a threshold value.

Having been informed of this, the comparing/determining circuit 65 outputs again the previous threshold value for R wave detection trigger, which has been sent from the threshold value determining circuit 6 to the comparator 55, to the comparator 55 (ST22). That is, as illustrated in FIG. 16, the process ends without the process of determining a threshold value for R wave detection trigger described with reference to FIGS. 13 and 14.

As described above, the threshold value determining circuit 6 checks whether the waveform, which is used for setting a threshold value for detecting the heart rate used as a reference value and the number of R wave detection triggers, contains noise before determining the threshold value for R wave detection trigger. Thereby, the threshold value determining circuit 6 can output a more accurate threshold value to the comparator 55.

Thus, according to at least one embodiment described above, it is possible to reliably detect R waves in the ECG waveform used as a trigger for determining the phase of the heart cycle while reducing erroneous detection.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An electrocardiographic (ECG) waveform timing detector, comprising processing circuitry configured to:
   receive an ECG waveform obtained by measuring a subject;
   calculate a heart rate based on the ECG waveform;
   set a threshold value for detecting a peak from the ECG waveform;
   detect a number of peaks having a wave height higher than the threshold value from the ECG waveform;
   when the heart rate and the number of peaks do not match, set a new threshold value and detect a number of peaks having a wave height higher than the new threshold value; and
   when the heart rate and the number of peaks match, output a trigger signal for detecting an R wave in the ECG waveform by comparing the threshold value to the ECG waveform.

2. The ECG waveform timing detector of claim 1, wherein the processing circuitry is further configured to:
   when the heart rate and the number of peaks match, set a lower limit equal to the threshold value, increase the threshold value and compare the increased threshold value with the ECG waveform until the heart rate and the number of peaks do not match, and set an upper limit equal to an increased threshold value right before the calculated heart rate and the number of peaks do not match, and
   set the threshold value based on the lower limit and the upper limit.

3. The ECG waveform timing detector of claim 2, wherein the processing circuitry is further configured to determine a midpoint value between the lower limit and the upper limit as the threshold value.

4. The ECG waveform timing detector of claim 3, wherein, when the ECG waveform contains noise, the processing circuitry does not calculate the heart rate.

5. The ECG waveform timing detector of claim 4, wherein,
the processing circuitry sets a threshold value for each heartbeat, and
when not calculating the heart rate, the processing circuitry does not perform the setting of the threshold value, and reuses a previous threshold value most recently set.

6. The ECG waveform timing detector of claim 2, wherein, when the ECG waveform contains noise, the processing circuitry does not calculate the heart rate.

7. The ECG waveform timing detector of claim 6, wherein,
the processing circuitry sets a threshold value for each heartbeat, and
when not calculating the heart rate, the processing circuitry does not perform the setting of the threshold value, and reuses a previous threshold value most recently set.

8. The ECG waveform timing detector of claim 1, wherein the processing circuitry is further configured to increase the threshold value to set a new threshold value when the heart rate and the number of peaks do not match.

9. The ECG waveform timing detector of claim 8, wherein, when the ECG waveform contains noise, the processing circuitry does not calculate the heart rate.

10. The ECG waveform timing detector of claim 9, wherein,
the processing circuitry sets a threshold value for each heartbeat, and
when not calculating the heart rate, the processing circuitry does not perform the setting of the threshold value, and reuses a previous threshold value most recently set.

11. The ECG waveform timing detector of claim 1, wherein the processing circuitry is further configured to calculate the heart rate based on a plurality of ECG waveforms obtained immediately before determining the threshold value.

12. The ECG waveform timing detector of claim 11, wherein, when the ECG waveform contains noise, the processing circuitry does not calculate the heart rate.

13. The ECG waveform timing detector of claim 12, wherein,
the processing circuitry sets a threshold value for each heartbeat, and
when not calculating the heart rate, the processing circuitry does not perform the setting of the threshold value, and reuses a previous threshold value most recently set.

14. The ECG waveform timing detector of claim 1, wherein
the processing circuitry stores therein a plurality of ECG waveforms, and
the processing circuitry is further configured to set the threshold value based on the plurality of ECG waveforms.

15. The ECG waveform timing detector of claim 14, wherein, when the ECG waveform contains noise, the processing circuitry does not calculate the heart rate.

16. The ECG waveform timing detector of claim 15, wherein,
the processing circuitry sets a threshold value for each heartbeat, and
when not calculating the heart rate, the processing circuitry does not perform the setting of the threshold value, and reuses a previous threshold value most recently set.

17. The ECG waveform timing detector of claim 1, wherein, when the ECG waveform contains noise, the processing circuitry does not calculate the heart rate.

18. The ECG waveform timing detector of claim 17, wherein,
the processing circuitry sets a threshold value for each heartbeat, and
when not calculating the heart rate, the processing circuitry does not perform the setting of the threshold value, and reuses a previous threshold value most recently set.

19. The ECG waveform timing detector of claim 1, comprising:
an ECG waveform generating device;
an ECG waveform storage device; and
a comparator configured to compare the ECG waveform and the threshold.

20. A medical image diagnosis apparatus, comprising an electrocardiographic (ECG) waveform timing detector having processing circuitry, the processing circuitry of the ECG waveform timing detector configured to:
receive an ECG waveform obtained by measuring a subject;
calculate a heart rate based on the ECG waveform;
set a threshold value for detecting a peak from the ECG waveform;
detect a number of peaks having a wave height higher than the threshold value from the ECG waveform;
when the heart rate and the number of peaks do not match, set a new threshold value and detect a number of peaks having a wave height higher than the new threshold value; and
when the heart rate and the number of peaks match, output a trigger signal for detecting an R wave in the ECG waveform by comparing the threshold value to the ECG waveform,
the medical image diagnosis apparatus being configured to generate a medical image based on the trigger.

* * * * *